Figure 1:
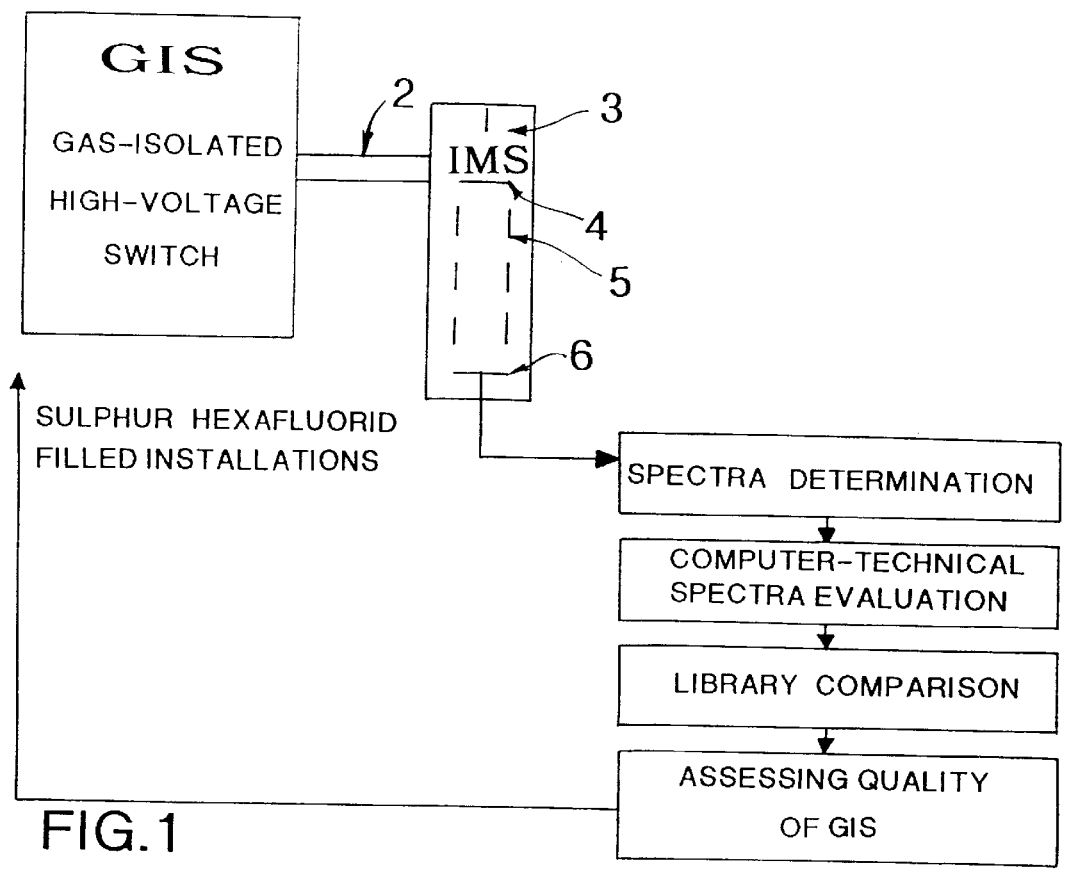

United States Patent [19]
Baumbach et al.

[11] Patent Number: 6,011,258
[45] Date of Patent: Jan. 4, 2000

[54] METHOD OF MONITORING THE QUALITY OF FILLER GASES, IN PARTICULAR SULPHUR HEXAFLUORIDE, IN GAS-FILLED INSTALLATIONS

[75] Inventors: Jörg Ingo Baumbach, Soest; Dieter Klockow, Dortmund; Michael Kurrat, Unna; Oliver Soppart, Hagen, all of Germany; Sandra Mara Alberti Segundo, Curitiba, Brazil

[73] Assignees: Gesellschaft zur Föderung der Spektrochemie und angewandten Spektroopie e.V., Dortmund, Germany; Laboratorio Central-Lac Convenio Copel e Ufpr, Parana, France

[21] Appl. No.: 09/011,488

[22] PCT Filed: Jul. 26, 1996

[86] PCT No.: PCT/EP96/03309

§ 371 Date: Apr. 30, 1998

§ 102(e) Date: Apr. 30, 1998

[87] PCT Pub. No.: WO97/05635

PCT Pub. Date: Feb. 13, 1997

[30] Foreign Application Priority Data

Aug. 2, 1995 [DE] Germany ............................ 195 28 290

[51] Int. Cl.[7] .............................. B01D 59/44; H01J 49/40
[52] U.S. Cl. ........................... 250/286; 250/288; 250/282
[58] Field of Search ..................................... 250/286, 282, 250/288, 287

[56] References Cited

U.S. PATENT DOCUMENTS 3,211,996  10/1965  Fox et al. .................................. 324/33
4,633,082  12/1986  Sauers ..................................... 250/282

FOREIGN PATENT DOCUMENTS 2414811   8/1979  France .
4130810  12/1992  Germany .

Primary Examiner—Edward P. Westin
Assistant Examiner—Nikita Wells
Attorney, Agent, or Firm—Brown & Wood, LLP

[57] ABSTRACT

A method of monitoring the quality of filler gases, in particular of sulfur hexafluoride ($SF_6$), in a gas-filled installation, in particular in gas-insulated switch units, such as high and medium voltage switches, a solution is provided which enables a continuous monitoring of the quality of filler gases in the gas-filled installation, which simultaneously enables to possibly determine the location of a fault and a type of the fault in such an installation. This is achieved by virtue of the fact that the filler gas of the installation, at least for the time of the analysis, is in a condition of a constant gas exchange with an ion-mobility spectrometer, in which the filler gas is ionized, and the ions are finally analyzed in the drift channel of the ion-mobility spectrometer.

9 Claims, 1 Drawing Sheet

METHOD OF MONITORING THE QUALITY OF FILLER GASES, IN PARTICULAR SULPHUR HEXAFLUORIDE, IN GAS-FILLED INSTALLATIONS

The present invention relates to a method of monitoring quality of filler gases, in particular of a sulfur hexafluoride ($SF_6$), in a gas-filled installation, in particular in gas-insulated switch units, such as high and medium voltage switches.

In gas-insulated high and medium voltage installations or containers, the filler gases are put in as insulation gases. At that, preferably sulfur hexafluoride ($SF_6$) is used because $SF_6$ combines a number of important characteristics which favors its use such as high insulation property, distinguished arc quenching characteristics, non-toxicity, high thermal and chemical stability, a small dielectric loss factor, high gas density, and favorable heat transfer characteristics. Though $SF_6$ has, under normal conditions, a constant chemical bonding, high thermal loads and electrical discharges destroy the $SF_6$ molecules. Gas-insulated switch units, therefore, provide for a qualitative retaining of insulation. However, during an operation, one cannot insure that this gas would not decompose if suitable counter-measures are not taken. This decomposition can be caused, e.g., by overheating at a connection location. Partial discharges on defected screen electrodes or direct gas breakdowns should be avoided. The decomposition products produced in this way are partially very high toxic and very corrosive. In addition, they adversely affect the electrical strength of the $SF_6$ insulating gas in switch apparatuses and installations which, together with increasing dissipation of the installation-filling gas determines the operational reliability of distribution of electrical energy.

These exemplary and known negative effects on the insulating property of the $SF_6$ gas require that very high standards be observed during the manufacture of the $SF_6$ installations and a constant monitoring of the insulating gas. It is known that despite high manufacturing quality and the undertaken measures such as fitting in of molecular sieves or absorption fitters in the installation in order to tie up water or gaseous decomposition products, long-life characteristics of the installation can deteriorate. Thus, e.g., partial discharges in gas-insulated switches can be measured directly. Because the formation of gaseous decomposition products worsens the electrical strength of a $SF_6$ installation, the quantative data about the electrical strength of $SF_6$ gas with decomposition products is of a big interest for power suppliers as operators of such an installation. The same is true for numerical values of reduction of the withstand voltage of the pin insulators under the influence of the humidity and the decomposition products. These data are indispensable for a gas diagnostics, e.g., for determining the time point of a gas exchange or of an event controlled revision as a long-range objective. A further planned use of the gas diagnostics is determining the fault location and the type of the fault. The fault location is found based on concentration differences in separate selected regions of the installation. The type of the fault can be determined from separate components of the decomposition products. Quantitative data related to the electrical strength of $SF_6$ gas including impurities of its decomposition products are obtained from experiments with a direct current corona discharge in a scientific apparatuses and off-line sampling and analysis in electrical switch units. To this end, test tubes for the web chemical method and the Fourier-transform-infrared spectroscopy as well as mass spectrometry are used. Conclusions based on acoustic methods with regard to the quality of the isolation gas are labor-consuming and instrumentation-consuming, are not completely precise and, at that, are relatively expensive. All of the above-mentioned methods are gas analytic laboratory methods, which are highly delicate and have a good selectivity, are off-line methods and, therefore, can indicate the operational condition of an installation only with a time delay. In addition, they are both labor-intensive and costly.

The object of the invention is, therefore, monitoring of the quality of filler gases in a gas-filled installation which would enable to determine the fault location and the type of a fault in such an installation.

According to the invention, this object is achieved by a continuous exchange at least at a time of analyses, of the filler gas of the installation with an ion-mobility spectrometer in which the filler gas is ionized and finally analyzed in the drift channel of the ion-mobility spectrometer. The use of the ion-mobility spectrometer for other purposes has been known for a long time. This apparatuses for some years have been designed and manufactured for use for military and civil purposes. Nowdays, the ion-mobility spectrometer is primarily used as a warning apparatus for chemical warfare products. Different scientific works describe the mobility of different negative and positive ions, which are primarily formed in $SF_6$, at different temperatures and pressures. However, here, the pressures are not comparable with operational pressures in high-voltage switches (P. L. Peterson, Mobilities of Negative ions in $SF_6$, J. Chem. Phys. 53 (1970) 694–704), and the temperatures are much higher than in the $SF_6$-filled installations. (S. N. Lin, G. W. Griffin, E. C. Horning, W. E. Wentworth, Dependence of Polpyatomic Ion Mobility on Tonic Size, J. Chem. Phys. 12 (1974), 94494–44999), or the electrical strength does not correspond to that in the ion-mobility spectrometers (J. de Urquijo-Carmona, C. Cisneros, J. Alvarez, Measurement of Tonization, Positive Ion Mobility and Longitudinal Diffusion Coefficients in $SF_6$ at High E/N, J. Phys. D:Appl. Phys. 18 (1985) 92017–2022).

The method according to the present invention makes possible a continuous and reliable monitoring of a quality condition of an industrial $SF_6$-filled installation. Ion-mobility spectrometry is a method in which the ions are supplied, under ambient pressure, by direct ionization or ion-molecular reactions and are then analyzed in the drift channel. The time which the ions require to produce a certain track in the drift channel, under the influence of an electrical field, is primarily a function of the mass and the charge of the ions. In addition, a certain role is played by the charge distribution in the molecule and by polarization.

An ion-mobility spectrometer can be so adapted, continuously or temporarily, to a gas-filled installation, which it bypasses that the spectra in the millisecond range of the examined mixtures can be taken and then evaluated in a suitable manner. Here, the observed difference between the spectrum of a pure $SF_6$, which practically corresponds in the filled installation to the spectrum contained in the middle, and the actual spectrum is used. In the spectrum, separate ions can be selected as conductive components. When in the course of an operation of a gas-filled installation, a change in the quality of the filler gas occurs, then the ion-mobility spectrum would change. Additional peaks can occur, dependent of the nature of the filler gas, its quality, its filling pressure, its water content, its oxygen content, and other parameters, or shifting of the peak position can take place. The course of the changes can be monitored and evaluated with computer assistance. Also, the quality of a purified $SF_6$ can be checked and monitored during refilling of the $SF_6$-filled installations.

Advantageously, the detected filler gas compound can be compared with a reference gas compound, and when a predetermined deviation from the reference gas compound is exceeded, a fault-signal is generated in order to signalize need for inspection and a danger of failure of the installation. As a reference gas naturally pure $SF_6$ is used.

In the ionization chamber of an ion mobility spectrometer, the primary ionization of gas molecules of the filler gas is effected with β-radiation, UV-radiation or with partial electrical discharge, with the latter being particularly advantageous.

According to a further advantageous embodiment, it is contemplated, when the ionization is effected by the electrical partial discharges, that the number and the duration of the partial discharges are so controlled with a series of electrical pulses that the initial pulses for an ion cluster directly coincides with the pulses of the partial discharges. In addition, the number of discharge carriers can be controlled, whereby preferable or intended ionization results are achieved, when a radioactive radiation source is used.

It proved to be particularly advantageous when a constant electrical field with a field strength between several 10 and several 100 up to several 1000 V/cm is established in the drift space of an ion-mobility spectrometer.

In order to insure a continuous monitoring, the ion-mobility spectrometer can be embedded in the gas-filled region of the installation or be in condition of a continuous gas exchange with the filler gas via a gas conduct (by gas flow and/or gas diffusion). Such gas exchange should be present or established at off-line and/or on-side operation, e.g., when periodical monitoring takes place.

It proved to be particularly advantageous for effecting the above-described process when an ion-mobility spectrometer has a rod-shaped ionization source located in the ionization chamber and a plate-shaped collector electrode at the end of the drift chamber (point-plate arrangement). In this way, the ions can be provided in the carrier gas $SF_6$ directly in the reaction chamber by a partial discharge, whereby a constant gas exchange between the filler gas of the installation and the ion-mobility spectrometer can be so established that a continuous measurement, at least for the time of analysis, becomes possible.

It proved to be particularly advantageous when the drift chamber is formed as a cylindrical tube, with the drift chamber being advantageously formed of a plurality of conductive electrode rings separated by insulated intermediate rings. Such an electrode arrangement is basically disclosed in DE 41 30 810 Cl.

Figure 2:
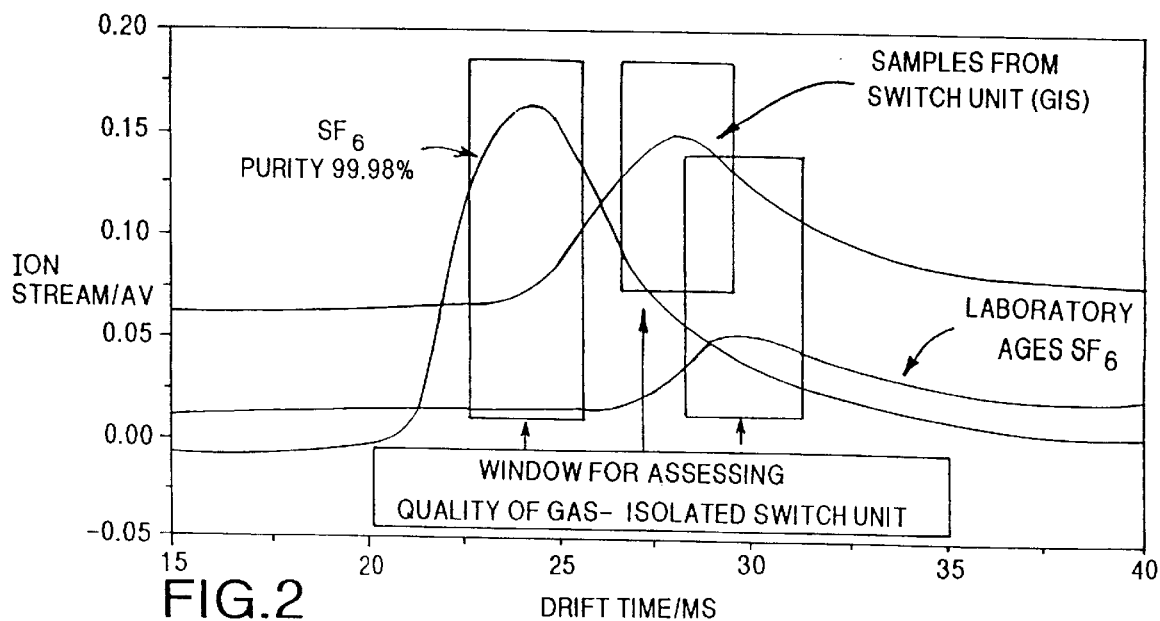

Now, the invention will be explained in detail below with reference to the drawings. The drawings show:

FIG. 1 a schematic diagram of a gas-insulated high-voltage switch equipped with an ion-mobility spectrometer; and FIG. 2 a diagram of comparison of ion-mobility spectra for negative ions in sulfur hexafluoride for pure $SF_6$ for a sample from an actual switch unit and for a laboratory-aged gas.

FIG. 1 shows a simplified view of a gas-insulated high-voltage switch designated as GIS. This high-voltage switch is connected, by a suitable connection 2, with an ion-mobility spectrometer IMS for enabling gas exchange therebetween. The ion-mobility spectrometer JMS has a rod-shaped ionization source 3 which is arranged in an ionization chamber with is bounded at the other end by a switch grid 4 for forming ion clusters. A further grid, not shown, can be arranged between the ionization source 3 and the switch grid 4. The switch grid 4 is adjoined by a drift tube 5 having a tubular shape and formed of a plurality of conductive electrode rings separated with insulated intermediate rings, respectively. At the other end of the drift tube 5, a Faraday plate 6, which functions as a collector electrode, is arranged.

In order to establish a uniform drift field of a suitable strength along the axis of the conductive electrode rings, the conductive electrode rings can be connected to a suitable potential. This potential is generated by a high-voltage source and, as a rule, is adjusted by a suitable resistor chain or resistor network. The strength of the electrical field is in order of several 100 V/cm along the drift path.

The strength of the electrical field in ionization chamber need not necessarily correspond to that in the drift chamber. An aperture grill is (not shown in the drawings) is provided in front of the Faraday plate 6 (the collector electrode).

Usually, a carrier gas with sample molecules, here decomposition products in the carrier gas $SF_6$ is supplied into the ionization chamber of the ion-mobility spectrometer IMS. This can be effected through the suitable connection 2 by a continuous gas exchange with the $SF_6$-filled installation GIS by way of gas transfer (gas flow or gas diffusion).

In the ionization chamber of the ion-mobility spectrometer IMS, carrier gas and analysed gas ions (decomposition products) are formed by using a radioactive radiation source, a UV-light source, or corona discharge, or particularly preferable a partial discharge. In the reaction region, as a rule, there is provided such electrical potential gradient, that the charged mixture of different ions is displaced toward the injection grill. For forming ion clusters, a switch grid 4 is located at the outlet of the ionization chamber. It opens periodically, e.g., every 50 ms for several 10 to 100 $\mu s$; normally, however, the passage to the drift cell is closed. From the adjacent outer electrical field, during the time the grid is open, a certain amount of ion mixture flows into the drift chamber 5. The outer electrical drift field, which is maintained substantially constant and has, in an ideal case, a linear potential gradient, causes a rapid drift of the ions, which may have different mass and structure and which move through an aperture grill, not shown, at the end of the drift chamber toward the collector electrode (Faraday plate 6). In a favorable case, completely separated partial ion clusters are located on the Faraday plate 6 where an ion-mobility spectrum can be obtained with a suitable amplifier and a display means. Here, the dependence of the time of arrival of the ions on their mobility is used. Thus, lighter ions reach the Faraday plate 6 earlier than heavier ions.

The possibility of on-line monitoring of the quality of $SF_6$ gases in the gas-insulated high-voltage switch GIS is based on the fact that ions can be made directly available in carrier gas $SF_6$ in the reaction chamber by partial discharge, advantageously with a point-plate device shown in FIG. 1, and on the fact that a continuous gas exchange between the filler gas of the high-voltage switch GIS and the ion-mobility spectrometer IMS can be so established that a continuous measurement becomes possible. Here, the difference between the spectrum in a pure $SF_6$, which is maintained in the middle of the filled installation, and the actual spectrum is utilized. At that, single ions can be screened in the spectrum as conductive components. When during the operation of the gas-filled installation, the quality of the filler gas changes, the ion-mobility spectrum also changes. Additional peaks can occur dependent on the nature of the filler gas, its quality, its pressure, its water content, its oxygen content, and other parameters. Alternatively, the peak position can change. The change course can be monitored and determined with computer assistance. When the set threshold values for a corresponding installation are exceeded, a need for inspection is signalized, and the danger of a failure of the installation and/or the switch GIS is displayed and, if necessary, an alarm is triggered.

FIG. 2 shows typical spectra, which occur in practice, namely, a curve for pure $SF_6$ (purity 99, 98%), for a sample from a real gas-insulated high-voltage switch GIS, and for a sample of laboratory-aged and, therefore, very damages $SF_6$. The differences are clearly recognizable, in particular, in the shift of the peak maximums, which makes possible to evaluate the quality of the $SF_6$ gases.

Naturally, the method according to the invention can be used not only for monitoring the quality of $SF_6$ but also for other gases.

We claim:

1. A method of monitoring the quality of filler gases, in particular sulfur hexafluoride ($SF_6$) in gas-filled installations, in particular in gas-insulated switch units such as high and medium voltage switches, characterized in that the filler gas of the installation, at least for the time of analysis, is in a condition of a continuous gas exchange with an ion-mobility spectrometer in which the filler gas is ionized and, finally, is analyzed in a drift channel of the ion-mobility spectrometer.

2. A method according to claim 1, characterized in that the already detected filler gas composition is compared with a reference gas composition and when a set deviation from the reference gas composition is exceeded, an error signal is generated.

3. A method, according to claim 1, characterized in that a primary ionization of gas molecules of the filler gas is effected in an ionization chamber of the ion-mobility spectrometer by β-rays, UV-rays or by an electrical partial discharge.

4. A method according to claim 3, characterized in that during the ionization by an electrical partial discharge by a series of electric pulses, the number and the duration of the partial discharge is so controlled that the initial pulse for an ion cluster directly coincides with the pulse of the partial discharge.

5. A method according to claim 1, characterized in that a constant electrical field having a field strength between several 10 and several 100 to 1000 V/cm is established in a drift chamber of the ion-mobility spectrometer.

6. A method according to claim 1, characterized in that the ion-mobility spectrometer is embedded in a gas-filled region of the installation or is in condition of a continuous exchange with the filler gas via a gas conduit.

7. An ion-mobility spectrometer for effecting the method according to claim 1, characterized in that it comprises a rod-shaped ionization source (3) in the ionization chamber and a plate-shaped collector electrode at the end of the drift chamber(s) (point-plate device).

8. AN ion-mobility spectrometer according to claim 7, characterized in that the drift chamber (5) is formed as a cylindrical tube.

9. An ion-mobility spectrometer according to claim 8, characterized in that the drift chamber (5) is formed of a plurality of conductive electrode rings separated with insulation intermediate rings, respectively.

* * * * *